United States Patent [19]
Haslbeck et al.

[11] Patent Number: 5,100,780
[45] Date of Patent: Mar. 31, 1992

[54] MEMBRANE PERFUSION METHOD AND APPARATUS FOR DETERMINING DOSE RESPONSE RELATIONSHIPS FOR SOLUBLE BIOLOGICALLY ACTIVE CHEMICAL AGENTS RELEASED FROM A SURFACE

[75] Inventors: Elizabeth G. Haslbeck, Annapolis, Md.; William C. Banta, Washington, D.C.; George I. Loeb, Bethesda, Md.

[73] Assignee: The United States of America as represented by the Secretary of the Navy, Washington, D.C.

[21] Appl. No.: 359,180

[22] Filed: May 31, 1989

[51] Int. Cl.$^5$ .............................................. C12Q 1/18
[52] U.S. Cl. ...................................... 435/32; 435/29; 435/291; 422/53; 422/68.1; 422/101
[58] Field of Search .................... 422/53, 56, 101, 261, 422/681, 256, 258; 435/283, 285, 291, 29, 32; 436/536

[56] References Cited

U.S. PATENT DOCUMENTS

| | | | |
|---|---|---|---|
| 2,940,360 | 6/1960 | Carter | 435/283 |
| 4,228,243 | 10/1980 | Iizuka | 435/285 |
| 4,296,205 | 10/1981 | Verma | 435/285 |
| 4,618,586 | 10/1986 | Walker | 435/283 |
| 4,629,686 | 12/1986 | Gronberg | 435/283 |
| 4,748,124 | 5/1988 | Vogler | 435/285 |

*Primary Examiner*—Christine Nucker
*Assistant Examiner*—Jeffrey Stucker
*Attorney, Agent, or Firm*—Howard Kaiser; Luther A. Marsh; John Stowe

[57] ABSTRACT

A membrane perfusion apparatus and method for determining the effective release rates of soluble biologically active chemical agents from a surface. A test cell houses a porous membrane so as to expose one surface of the membrane to a fluid containing at least one organism potentially reactive with a chemical agent of interest being perfused through the membrane at predetermined rates. In the context of antifoulant chemical agents, the invention permits the determination of the minimum effective release rates for biocides.

40 Claims, 2 Drawing Sheets

MEMBRANE PERFUSION METHOD AND APPARATUS FOR DETERMINING DOSE RESPONSE RELATIONSHIPS FOR SOLUBLE BIOLOGICALLY ACTIVE CHEMICAL AGENTS RELEASED FROM A SURFACE

The invention described herein may be manufactured and used by or for the Government of the United States of America for governmental purposes without the payment of any royalties thereon or therefor.

BACKGROUND OF THE INVENTION

1. Field of the Invention

The present invention relates to an apparatus which allows surfaces to be perfused with a soluble biologically active chemical agent at controllable flux rates, and a method for determining the effects therefrom; particularly, but not exclusively, biocidal agents meant to be incorporated in antifouling coatings and coverings.

2. Description of the Prior Art

Improvements in ship hull design over the past years have been aimed at maximizing vessel speed and range by minimizing hydrohynamic drag. In order to take full advantage of these improvements the hull must remain smooth, that is, clean and free from fouling organisms. Marine fouling increases hull roughness and therefore drag which leads to inncreased fuel consumption and decreased overall efficiency of the vessel.

The accumulation of fouling organisms on buoys, pier pilings, discharge pumps, ship hulls, propeller blades, hydrofoil legs, and the like greatly increases maintenance costs, and may adversely affect function which may constitute a source of danger, particularly when affected sites are necessary for normal operation. In the case of a sonar dome, which ideally has a smooth rubber surface, a layer of fouling organisms tends to deflect and scatter the sonar beams.

The prior art illustrates a number of combinations of paint and polymeric materials containing biocidal agents which prevent accumulation of fouling organisms. For example, antifouling coverings using rubber which contains organometal toxicants as a reservoir layer onto which is laminated an elastomertic layer that serves as a toxic transfer control sheet are exemplified in U.S. Pat. Nos. 3,426,473, 3,497,990, 3,505,758, and 4,401,703. The most prevalent biocidal agents used in modern antifouling coatings are copper and organotin compounds.

Antifouling coatings are designed to release biocides over several years at a controlled rate. The biocides are released from their binder materials by film erosion, ablation, and/or diffusion and prevent attachment of fouling organisms or kill them before they grow to significant size. Various polymeric binder compounds have been developed in an effort to control the release rates of these toxicants as exemplified, by way of example, in U.S. Pat. Nos. 3,016,369, 3,382,264, 3,930,971, 3,979,354, 4,064,338, 4,075,319, 4,174,339, 4,389,460, and 4,480,056. However, many of these older diffusion-dependent coatings exhibit a characteristic decrease in toxicant release rate where initial release rates are very high but decrease with time. After decreasing, this rate must be sufficient to control the target marine growth. Therefore, formulations designed for long life may have unacceptably high initial release rates.

Studies conducted by the Environmental Protection Agency (EPA), the U.S. Navy, and others have indicated that concentrations of organotin currently in the waters of the United States may pose unreasonable risks to oysters, clams, fish, and other aquatic life forms. There is increasing evidence to suggest that the excessive release of powerful biocides, such as tributyltin (TBT), from antifouling coatings may cause environmental damage. While coatings based on organotin compounds have proven more effective in inhibiting marine growth than the conventional copper-based coatings, the organotin biocide can affect non-target marine and freshwater organisms. This is of particular concern when many ships are berthed near areas which contain economically significant organisms. For example, TBT is toxic to Pacific oysters (*Crassostrea gigas*) at very low levels; slow growth and high mortality occur at concentrations as low as 0.05 $\mu g/L$.

In an effort to protect the aquatic environment, Great Britain, France, the United States, and others have imposed legislative restrictions on the use of organotin paints. The U.S. Congress has passed the Organotin Antifouling Paint Control Act of 1987 prohibiting the use of organotin antifouling paints on vessels less than 25 meters in length. This Act requires the Administrator of the EPA to certify each antifouling paint containing organotin to be at release rates of not more than 4.0 micrograms per square centimeter per day, as determined by the Americal Society for Testing Materials (ASTM) standard test method which the EPA required in its July 29, 1986 data call-in notice or by any similar test method specified by the Administrator. The Act also instructed the EPA Administrator and the Secretary of the Navy to conduct research into chemical and non-chemical alternatives to antifouling paints containing organotin. Under these circumstances it is highly desirable to develop effective antifoulant coatings with lower, more precisely controlled release rates.

Paint manufacturers have therefore improved coating formulations by developing organometallic polymer coating systems based upon organometal acrylate polymers which demonstrate a constant delivery rate of the toxicant. Binding TBT to a polymer is effective in regulating the release rate of the biocide from the organometallic polymer coating. Since toxicant release in these systems depends on a hydrolysis and lixiviation process, some formulators have concentrated on varying the polymer characteristics in order to control the erosion rate, as evidenced, for example, by U.S. Pat. Nos. 4,075,319 and 4,082,709. Others, however, have included hydrophobic additives such as chlorinated rubbers, polyacrylate esters, and silicones to retard and control release, as evidenced, for example, by U.S. Pat. No. 4,021,392. In addition, alternatives to organometals, such as the natural compounds from whip corals that appear to prevent biological attachment, are currently being isolated by researchers at Duke University and the University of Delaware.

However, as constitutent coating materials are developed which tend to produce steady state release rates, little scientific data exists as to what minimum release rate will be effective for control of target organisms. Although it is not precisely known how rapidly organotin compounds, such as TBT, must be released in order to be effective against fouling organisms, there is evidence that current antifouling paint release rates are several times higher than necessary to prevent significant fouling. It would therefore be useful to determine the minimum release rate of organometallic and other biocides in order to reduce environmental damage without decreasing the effectiveness of antifouling coatings.

Minimizing the threat to non-target organisms requires controlling and minimizing the biocide release rate to only that level which is sufficient to prevent attachment. Determining optimum release rates by current methods requires that an array of paint formulations be developed and tested for their release rate and antifouling effectiveness. Formulating and testing new antifouling paints to a minimum or optimum release rate would be desirable, but is a difficult, expensive, and time-consuming process. In this field, it would be useful to have an estimate of a toxicant's minimum effective release rate before the formulation process begins. That is, the ability to determine an optimum biocide release rate under natural conditions would greatly facilitate the development of effective antifouling coatings whose environmental impacts are negligible.

SUMMARY OF THE INVENTION

The present invention provides an apparatus for releasing, at at least one known release rate, at least one soluble biologically active chemical agent from a surface into a fluid containing at least one organism potentially reactive with at least one said chemical agent, and a method for determining the effect, at each of at least one known release rate from a surface into a fluid, of at least one soluble biologically active chemical agent which is released from the surface into the fluid, upon at least one organism in the fluid. Herein, a fluid-tight test cell houses a porous membrane so as to expose one surface of the membrane. A flow regulation device perfuses a solution containing the agent of interest through the membrane at predetermined rates for a fixed period of time. A fluid containing at least one organism potentially reactive with said perfused chemical agent is introduced past the exposed surface of the membrane. By knowing the flow rate and varying the concentration that said chemical agent is being perfused, one is able to observe the reaction of said organism and determine said chemical agent's effective release rate.

In the context of antifoulant biocidal chemical agents, the method and apparatus of the subject invention will permit determination of the minimum effective release rates for conventional biocides by providing data which is used to develop a dose-response graph and toxicity curve for each particular agent. This invention will also make possible the test of new, and/or more environmentally compatible, antifoulants and their combinations, by determining the optimum release rates that are effective in preventing fouling biological growth prior to coating formulation.

Accordingly, it is an object of this invention to provide a method and apparatus that allows determination of the effective release rate of soluble biologically active chemical agents from a surface.

It is also an object of this invention to provide a method and apparatus that allows the minimum effective release rate of a biocide to be determined without the need to formulate a variety of different antifoulant coatings or coverings.

It is a further object of this invention to provide a method and apparatus which is used to determine any synergistic effects among combined toxicants or between antifouling compounds and other coating constituents.

BRIEF DESCRIPTION OF THE DRAWINGS

In the figures, like reference numerals designate like or corresponding components throughout the several views.

DETAILED DESCRIPTION OF THE INVENTION

Hull husbandry and ship maintainance programs require antifoulant protection which is effective in preventing the accumulation of fouling organisms on submerged and surfaces yet is compatible with environmental constraints. The apparatus and method of the present invention will allow the determination of the effective release rates of soluble biologically active chemical agents from a surface. Specifically, the present invention is useful in determining the minimum effective release rates of various biocides to be included in antifouling coatings and rubber coverings prior to the time at which samples of these materials are formulated for testing.

Figure 1:
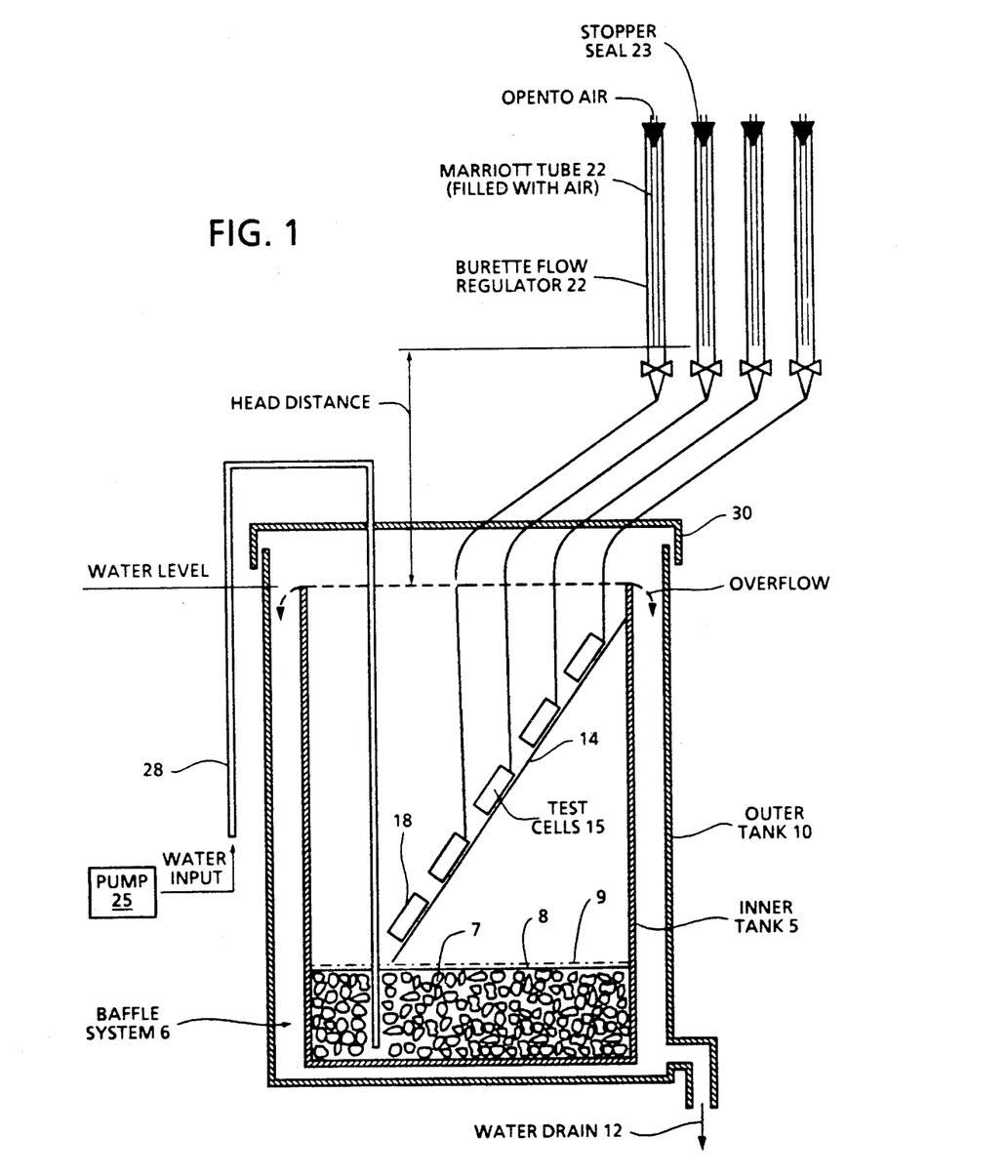
FIG. 1 illustrates an example of a laboratory set-up for use of the present invention apparatus.

FIG. 1 illustrates one example of the invention apparatus set-up for laboratory use which accomplishes this end by having a double wall and bottom reservoir type construction. The inner tank receptacle 5 is surrounded by but separated from a larger outer tank enclosure 10. The outer enclosure 10 is fitted with a drain outlet 12 at its bottom and has sidewalls which exceed the height of the inner receptacle 5 so that when a fluid medium is introduced into tank 5, fluid overflow is confined to the interstitial wall space for exit at 12. Means 25 for controllably introducing said fluid containing the fouling organisms is provided external to receptacle 5 and is connected thereto by pipe 28. A baffle system 6 is provided at the bottom of the inner receptacle 5 so as to dissipate turbulence and disperse gas bubbles introduced at this level by said piping 28, said baffle system equalizing the current flow throughout the entire diameter of the inner tank. Since the rate of supply from component 25 is variable, supply should be provided at a rate which best simulates the standard movement of the fluid for the condition to be studied. A rack 14 which holds at least one test cell 15 in place is positioned above the baffle system 6 in the inner tank receptacle 5. These test cells 15, an exploded perspective view of which is shown in greater detail in FIG. 2, act as microporous membrane 13 holders and are each, save one which may function as a no-flow control 18, connected by tubing 24 to flow regulator devices 20 capable of delivering chemical agents at predetermined rates to said test cells 15. The outer enclosure 10 may optionally be fitted with a tank top cover 30 to prevent sunlight from penetrating the fluid. All components of the apparatus which are in contact with the chemical agent should be selected from material which are impervious to absorption of and/or are otherwise unreactive with the particular chemical agents to be tested.

It should be recognized that the apparatus heretofore described would be equally functional, without the double tank 5 and 10 and baffle 6 and means 25 components, if a test cell 15 rack 14, fed by 20, were directly submersed in, for example, a flowing marine environment. Further, while the present invention will be discussed in the context of antifoulant protection, it should be understood, in light of this disclosure, that the apparatus is useful in any field where it is desirable to simulate the release rate of a soluble biologically active chemical agent perfused from a surface. The chemical agent's effect on any organism in the fluid which flows past the surface, as represented by the membrane, is then directly observable.

Figure 2:
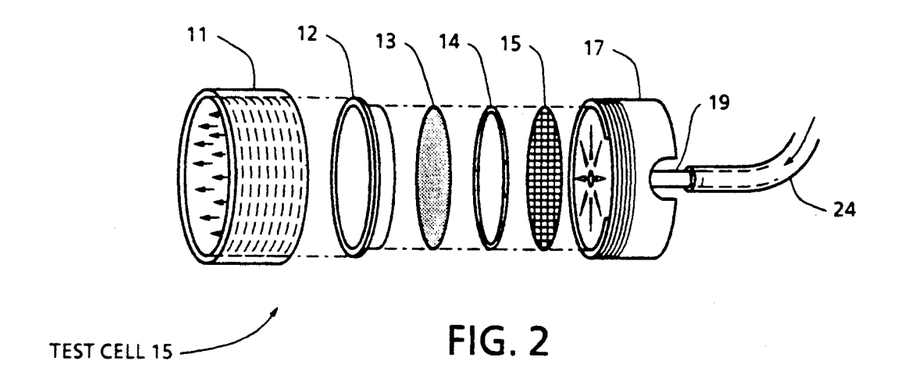
FIG. 2 is an exploded perspective view of a test cell assembly.

Initially, use of this apparatus requires determination of chemical agent delivery rates that will not influence the settlement of fouling organisms. The upper limit for solution delivery from regulator 20 is established by passing filtered water, obtained from the same source as is used to supply tank 5, through the test cell's 15 membranes 13 at different flow rates and noting the amount of fouling as compared to the no-flow control cell 18 membrane 13. Since all of the test cells are placed directly into a constant supply of liquid containing various marine organisms, one has isolated the flow rate from 20 as a variable in order to evaluate its effect on membrane attachment for all of the fouling organisms present at that location. This information is used to determine the range of acceptable flow rates for use with the chemical agents to be subsequently tested. Various solution concentrations of the biocide(s) are then prepared and perfused at these predetermined flow rates through the active test cell's 15 membranes 13.

Threshold release rates are determined by perfusing solutions containing a known concentration of the chemical agent through the test cell's 15 membrane 13 at the predetermined flow rates. As seen in FIG. 2, the downstream face of the membrane is exposed to the fluid medium and is available for attachment of fouling organisms. The flow regulation device 20 allows for precise reproducible control of the flux of chemical agent through membranes 13 and simulates the conditions of an antifouling coated surface—with a flow of the chemical agent from the surface of the material. By changing the concentration of the chemical agent in solution passed through the membrane, any desirable release rate or flux, defined here as the flow rate ($ml/cm^2/hr$) times the agent concentration ($\mu g/ml$), can be achieved. In this manner, it is possible to test any dispersible chemical agent or combinations of agents by simply changing the test solution. Various candidate booster biocides can also be tested to find the most effective combination and concentration ratio against biofouling. This permits a great deal of flexibility for determining the synergistic effect of toxic agent combinations and optimizing desirable biocide ratios.

Thus, the flux of the biocide in solution delivered by 20 is varied to estimate the minimum release rate that will be effective in suppressing fouling organism development. Of clear importance is the flux or dose levels that are to be used. Clearly, the concentrations should be ones that elicit detectable responses. They should not be so high as to prevent attachment of all the organisms, nor so low as to have no effect. When the biocide is not well known in advance, some searching is necessary in order to establish parametric values for the concentrations. Once a flux range of interest has been determined, that is, predetermined flow rates which do not affect organism settlement and a minimum and maximum concentration, one must decide how to distribute the number of experimental observations to be taken across this range. When interpreting the results from the test runs, flux levels or dose values on each end of the range serve to decrease the variance of the model form used to fit the data generated. Values in the middle serve primarily to assess "lack of fit", that is, whether one has chosen the correct line form for the toxicity model. A fairly conservative approach would be to use one-third of the values on the low end of the range, one-third on the high end and one-third evenly spread across the range. At a minimum, three values should be used between the high and the low values. Use of three data points allows for one of the interior points to be unreliable and still serve to distinguish a curvilinear from a linear model form.

With the flow rates and concentration parameters established, test runs are conducted varying the chemical agent's flux rate. Fouling organism densities present on the active test cell's 15 membranes 13 are evaluated relative to the population present on the control cell 18 membranes 13. Data is taken for each dose test run. After the data is statistically analyzed, a dose-response graph and toxicity curve can then be prepared for the chemical agent, comparing flux ($\mu g/cm^2/day$) versus the logit of the surviving fraction (organism test cell density fraction relative to controls). For the particular biocide tested, this enables one to predict within a given confidence limit, depending upon the criteria set for failure, that is, the survival fraction desired, the minimum effective release rate necessary to achieve that level of fouling control.

By way of example, but not by way of limitation, the following test which was conducted at Annapolis, Md. in the Severn River specifically demonstrates the method of use of the disclosed apparatus:

EXAMPLE 1

Modern organotin biocides are successful in controlling hard foulers such as barnacles and bryozoans, but are not effective in controlling microbial biofolms composed of organisms such as bacteria, diatoms, algae and protozoans, which are more resistant. Surfaces covered by microbial biofilms, with no hard foulers present, have drag increased by as much as 10% over that of clean hull surfaces.

A group of ciliated protozoans called peritrichs are an important part of the biofilm that occurs in the Chesapeake Bay area. They attain significant populations on submerged surfaces within a day. Peritrichs attach to surfaces by a permanent stalk, 100–500 μm in length, which supports a single peritrich or colony, 30–100 μm in diameter. As the largest part of this organism occurs well above the substratum, organisms in this form may contribute significantly to vessel drag. Biofilms not only increase fuel consumption because of increased drag, but may also damage both AF and anti-corrosive coatings. Peritrichs were found to be a major constituent of fouling organisms from experimental panels coated with a modern tributyltin (TBT) antifoulant paint submerged in the Severn River.

The marine system source in this case was an estuary of the Severn River which is brackish with a salinity content that ranged during the test period from 8–10 ppt. Oxygen concentrations were near saturation at approximately 6 ml/L. Water temperatures ranged from 6°–24° C., decreasing throughout the test period. The water in the Annapolis Harbor area contains background levels of TBT from about 10 to 31 μg/L, presumably released from antifouling paints on vessels in the Chesapeake Bay area.

Test cells 15 were made by modifying plastic filter holders designed for microfiltration. As can be seen in FIG. 2, the test cells for this demonstration were made from a modified 47 mm Swin-Lok® (a registered trademark of Nucleopore Corp. of Pleasanton, CA.) #420410 polycarbonate filter holder by removing the central 4 cm of the filter cap 11 with a grinding tool, thereby converting the cap into a ring. Aerosol holders, as for example, a 47 mm Swin-Lok® #430400 and others, designed for open system handling of air and other gases, may also be directly adapted to this use. The test surface was a thin, flat, circular polycarbonate membrane 13, 47 mm in diameter, with a 0.2 $\mu$m capillary pore size. It should be noted that all apparatus components in contact with the test solution were composed of either polycarbonate, fluorinated ethylene propylene (FEP) Teflon® (a registered trademark of E. I. DuPont of Wilmington, DE.), or tributyltin-saturated glass—as these materials do not react with or absorb the agent to be tested. Membrane 13 was held in place on top by a locking ring 12 between the modified filter cap 11 and by an "O" ring 14 sealing the edge of the membrane to a baffle piece 16 below. The baffle piece 16, which assists in distributing the delivered chemical solution throughout membrane 13, together with 14, 13 and a portion of piece 12, fit inside the raised lip of the filter holder base 17, the exterior of which is threaded to fit the interior of the filter cap 11. When assembled, the modified liquid-tight filter holder is used as a test cell by connecting tubing 24 to the male Luer slip-fitting 19 on the filter holder base 17, exposing only a 41 mm diameter central area on one side of the membrane 13 to seawater.

A plurality of test cells 15 were mounted on a rack 14 of rectangular plexiglass plate provided with slots to hold the test cells. As can be seen from the laboratory set-up shown in FIG. 1, water was controllably introduced by pumping means 25 from a marine system source and entered from the bottom of an inner tank receptacle 5 at a constant flow rate of between 1-2 L/min. This water then passed through a baffle system 6 consisting of a 10 cm bed of rock 7 with an average diameter of about 3 cm, a plankton net 8 to direct gas bubbles away from the test cells and a horizontally mounted 30 cm diameter diffusion plate 9 of plexiglass perforated by 30 holes, each 5 mm in diameter, before encountering the test cell rack 14 resting on 9 and inclined against the sidewalls of tank 5. Seawater containing a natural population of organisms including peritrichs entered the bottom of the inner tank 5, passed through the baffle system 6, and overflowed the inner tank. The inner tank receptacle 5 emptied into a larger surrounding tank enclosure 10 from which the overflow was drained at 12. The tanks 5 and 10 were protected with a cover 30 of aluminum foil to reduce algal growth and prevent the possibility of light causing an uneven distribution of organisms in the tank. Flux of the selected toxicant through the test cell 15 membranes 13, defined as the flow rate times the concentration of the chemical solution, was controlled by delivering varying concentrations of the agent in solution at a constant flow rate through capillary tubing 24. Although various systems exist for delivery of the chemical solution at a constant rate, including the use of peristaltic pumps or other pressure devices, a constant hydrostatic head was produced here by elevating the solutions in a Marriott bottle arrangement as is shown in FIG. 1. This arrangement comprised a 100 ml glass burette flow regulator 20 which was sealed with a rubber stopper 23 through which passed a 2.5 cm length of fluorinated ethylene propylene (FEP) tubing 22. Air was admitted to the burette only through the FEP tubing, so the hydrostatic head became a function of the vertical distance between the bottom of the FEP tube 22 and the surface of the water level reached in tank receptacle 5. This distance and the diameter of the capillary tubing 24 were varied to produce the approximate flow rates desired. Actual flow rates were determined by measuring the volume of chemical solution delivered by the burettes 20.

For this experiment, a 0.0697 millimolar stock solution of tributyltin chloride (TBTCl) was selected to be tested and was prepared from the 95% oil by dissolving 0.0161 grams of TBTCl in 250 ml methyl alcohol. This stock solution was stored in the dark at 4° C. until use. As the smaller 0.11 mm interior diameter capillary tubing 24 utilized was subject to clogging, control and test solutions were required to be free of air bubbles and particulates. It was therefore necessary to pasteurize and filter the seawater used to make up the TBTCl solutions. Test solutions were prepared from the stock solution by serial dilution using filtered, 5 $\mu$m pore size, and pasteurized (for 30 minutes at 60° C.) seawater to yield the desired TBTCl concentrations in a 1% methanol solution. Control solutions were also 1% methanol.

Each experimental run included four flowing test cells 15 containing various concentrations of TBTCl solution and three controls 18—two control test cells flowing filtered seawater in a 1% methanol solution and one non-flowing control test cell. All test cells were exposed for approximately 24 hours. There was no detectable variation in flow rate during runs for test cells 15 whose flow rates were not interrupted by plugging of the capillary tube 24. Data from burettes 20 which did not flow properly were discarded. A one-way statistical analysis of variance (ANOVA) level determined that within runs there was no significant variation in peritrich densities between flowing and non-flowing control 18 test cells. Counts from these two types of controls were therefore combined.

After exposure, membranes 13 were fixed 1-7 days in 5% unbuffered formalin in filtered seawater. They were then stained 5 minutes in acetocarmine, rinsed with distilled water, placed on a 75×50 mm slide with five drops of immersion oil, and dried for 2 hours under vacuum at 40° C. A 48×60 mm #1 coverslip was applied and peritrichs were counted at 100× total magnification. A rectangular grid system was used to count peritrichs in 141 fields, each with an area of 1.99 mm$^2$. About 21% of the 1320.25 mm$^2$ total area of each exposed membrane 13 was examined. Table I below presents the data resulting from such peritrich population count.

TABLE I

Peritrich Population by Dose

| Flux g/cm$^2$/day | Run No. | Fields Examined | Peritrich Count | Mean Density | Surviving Fraction | Logit $\log\left(\frac{y}{y-1}\right)$ |
|---|---|---|---|---|---|---|
| 0.00 | 1 | 705 | 428 | 0.069 | 1.000 | |
| 0.00 | 2 | 705 | 1333 | 2.040 | 1.000 | |
| 0.00 | 3 | 423 | 2941 | 6.953 | 1.000 | |
| 0.00 | 4 | 423 | 4304 | 10.175 | 1.000 | |
| 0.00 | 5 | 423 | 6662 | 15.749 | 1.000 | |
| 0.00 | 6 | 423 | 2232 | 5.277 | 1.000 | |
| 0.00 | 7 | 1269 | 338 | 0.266 | 1.000 | |
| 0.39 | 1 | 423 | 195 | 0.461 | 0.758 | 0.50 |
| 1.15 | 7 | 423 | 31 | 0.073 | 0.275 | −0.42 |

TABLE I-continued

Peritrich Population by Dose

| Flux g/cm²/day | Run No. | Fields Examined | Peritrich Count | Mean Density | Surviving Fraction | Logit $\log\left(\frac{y}{y-1}\right)$ |
|---|---|---|---|---|---|---|
| 1.30 | 7 | 423 | 31 | 0.097 | 0.364 | −0.24 |
| 2.18 | 7 | 282 | 6 | 0.021 | 0.080 | −1.06 |
| 2.62 | 7 | 282 | 5 | 0.018 | 0.067 | −1.14 |
| 3.74 | 2 | 423 | 316 | 0.747 | 0.492 | −0.01* |
| 4.62 | 1 | 141 | 4 | 0.028 | 0.004 | −2.38 |
| 4.70 | 1 | 141 | 1 | 0.007 | 0.012 | −1.92 |
| 4.75 | 2 | 141 | 2 | 0.014 | 0.010 | −2.00 |
| 8.13 | 6 | 141 | 0 | 0.000 | 0.000 | |
| 8.19 | 4 | 141 | 4 | 0.028 | 0.003 | −2.52 |
| 8.85 | 6 | 141 | 1 | 0.007 | 0.001 | −2.99 |
| 9.66 | 4 | 141 | 1 | 0.007 | 0.001 | −2.99 |
| 13.50 | 5 | 141 | 4 | 0.028 | 0.002 | −2.69 |
| 15.30 | 5 | 141 | 4 | 0.028 | 0.002 | −2.69 |
| 15.89 | 4 | 141 | 3 | 0.021 | 0.002 | −2.69 |
| 16.82 | 3 | 141 | 47 | 0.333 | 0.048 | −1.30 |
| 16.92 | 3 | 141 | 3 | 0.021 | 0.003 | −2.52 |
| 18.95 | 4 | 141 | 0 | 0.000 | 0.000 | |
| 20.82 | 6 | 141 | 0 | 0.000 | 0.000 | |
| 23.06 | 3 | 141 | 0 | 0.000 | 0.000 | |
| 23.07 | 6 | 141 | 0 | 0.000 | 0.000 | |
| 24.74 | 1 | 141 | 0 | 0.000 | 0.000 | |
| 27.23 | 5 | 141 | 1 | 0.007 | 0.000 | |
| 31.38 | 5 | 141 | 0 | 0.000 | 0.000 | |

*Figure discarded by the criteria of Daniels et al infra

Significant slime films were present on both the running test cells 15 and control test cell 18 membranes 13 after 21 hours. The predominant organisms present in the preparations were species of ciliated peritrich protozoans; *Carchesium* sp., *Zoothamnium* sp., and possibly *Pseudocarchesium* sp. Other organisms including bacteria, protozoans, and a few diatoms were present. Many organisms not irreversibly attached to the substratum may have been lost in preparation of filter membranes for counting. However, peritrichs are attached to the substratum by a permanent stalk and no evidence of significant loss of peritrichs by stalk breakage was observed.

Peritrich densities varied widely on control 18 test cell membranes 13 from run to run, ranging from 12 to 1046 peritrichs/cm². The variability presumably was due to different exposure periods and variations in numbers and behavior of available larvae. While direct comparisons among the several runs were therefore difficult, within any particular run peritrich densities were strongly dependent on TBTCl flux. Therefore, comparisons among runs are possible by considering proportional reduction in peritrich densities from control 18 counts. The one-way ANOVA performed at the 5% level on the control 18 test cells demonstrates that no significant variation in peritrich populations resulted from variation in test cell location in tank 5.

Figure 3:
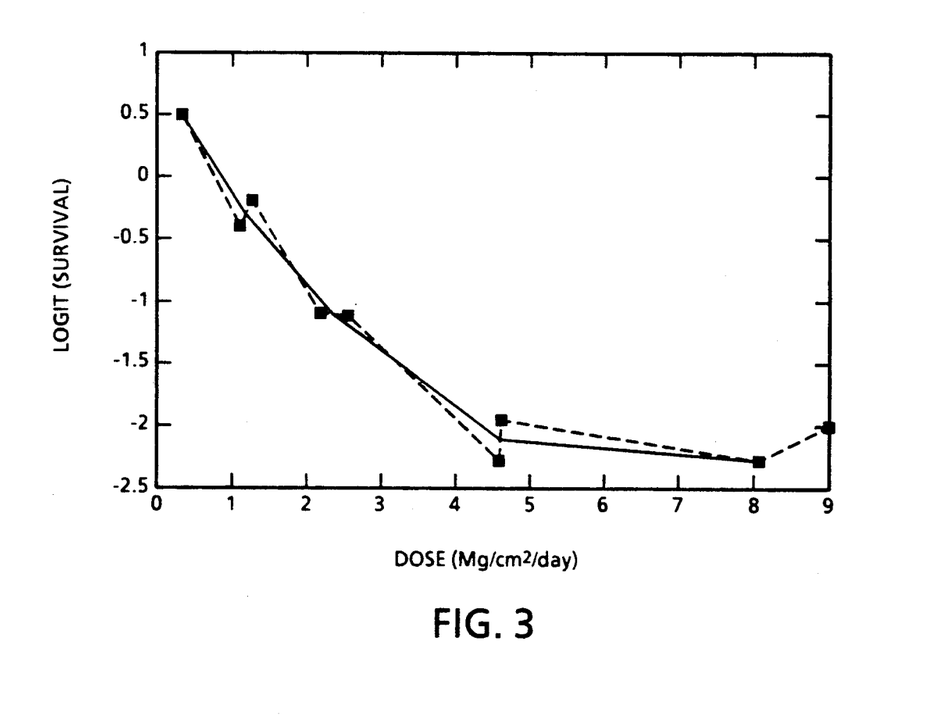
FIG. 3 is a dose-response graph exhibiting the toxicity curve for tributyltin chloride on peritrich protozoa.

From the Table I survival data, the general approach is to formulate a model for the relationship between survival and dose. The FIG. 3 toxicity curve is prepared by plotting the dose levels (or flux in µg/cm²/day) versus response (or logit of surviving fraction). The first control 18 values, representing 100% survival at zero dose levels for any given run, are used as the denominator when computing the peritrich survival fraction (peritrich density relative to control population expressed as a decimal percent). The usual model for survival as a function of dose is the logistic model. Hence, letting y(x) be the fraction that survive a given dose, x (where $0 < y < 1$). For graphic modeling purposes, we now define $p(y) = \log(y/1-y)$. Either common or natural logarithms may be used. Here, common logs have been taken. This gives the logit of y, or in Tukey terminology, the "flog" of y. When the observed y is either 0 or 1, some adjustment is necessary. In this analysis, we have taken such cases to correspond to y=0.005. FIG. 3 shows the graph of p=logit(survival) versus x=dose level. One extreme point, at flux=3.74, was discarded by the criteria of Daniels et al (*Experimental Physical Chemistry*, McGraw-Hill Company). Additionally, fluxes greater than about 8.19 µg/cm²/day substantially suppressed all peritrich growth, and were therefore not included in this statistical analysis.

It can be seen from the FIG. 3 graph that the relationship between p and x is distinctly quadratic. Therefore, a quadratic model was fit using unweighted least squares. The resulting equation is: p=0.7985−0.97695 x+0.073811 x². R² for this model is 0.986 and the estimated residual standard deviation is 0.136. FIG. 3 shows the dose-response data with the fitted quadratic superimposed in heavy line.

We next form the confidence bounds around this quadratic model. The objective here is to find a confidence interval on the required dose for a given level of toxicity. Since we wish a lower bound on the dose only, one-sided confidence intervals are used. In this analysis, a confidence interval for the mean response rather than for the predicted response was also used since the predicted response contains both uncertainty about the mean response as well as the variability of the response itself. If we let p' be the modelled value for a given dose x, the upper confidence interval for the mean response is: $p' + t\, S\, (x'(X'X)^{-1} x)^{\frac{1}{2}}$, where $(X'X)^{-1}$ is the inverse of the design matrix in accordance with Draper and Smith (*Applied Regression Analysis*, Wiley Enterprises). Table II below gives the upper confidence interval for the mean response at model doses.

TABLE II

Confidence Interval by Dose

| Flux µg/cm²/day | p' Modelled Value | Upper C.I. |
|---|---|---|
| 2.000 | −0.86 | −0.76 |
| 2.250 | −1.03 | −0.92 |
| 2.350 | −1.09 | −0.99 |
| 2.500 | −1.18 | −1.08 |
| 2.750 | −1.33 | −1.22 |
| 2.800 | −1.36 | −1.25 |
| 2.850 | −1.39 | −1.27 |
| 3.000 | −1.47 | −1.35 |
| 4.000 | −1.93 | −1.79 |
| 5.000 | −2.24 | −2.10 |
| 6.000 | −2.41 | −2.27 |
| 7.000 | −2.42 | −2.30 |
| 8.000 | −2.29 | −2.16 |

The confidence interval for a given dose is to be taken where these bounds intersect the desired level of toxicity. Note that the confidence interval is rather near p' for moderate doses and that the confidence interval flares upward for large doses. Therefore, within the upper confidence intervals given above, from FIG. 3, for a 10% peritrich survival rate, which corresponds to a logit of −0.9542, it can be seen that the required minimum TBTCl dose is 2.2 µg/cm²/day. Likewise, for a 5% protozoan survival rate, corresponding to a logit of −1.279, the minimum required dose would be 2.85 µg/cm²/day. For a 1% survival rate, which corresponds to a logit of −1.996, the required minimum effective dose of TBTCl alone would be about 4.35 $\mu g/cm^2/day$.

The test results presented in this application demonstrate use of the apparatus disclosed and a method designed to determine the minimum release rates of biocides which are effective in preventing the growth of fouling organisms. The membrane perfusion method can be used to deliver known quantities of any finely dispersable biocide if the agent is active in the dissolved state. With this method and apparatus, it will be possible to quantify optimum release rates of biocides independent of other coating constituents, thereby reducing the number of coating and/or covering formulations needed for trial testing.

The apparatus and method may be applied to the study of quantitative effects of any bioactive compound released from a surface, if the compound particle size has been sufficiently reduced so as to pass freely through the membrane. Other porous membrane materials may be suitable for different toxic agent solutions. Current investigations, for example, are now being conducted using this method and apparatus to test various slimicides, i.e., biocides targeted for microbial biofilm control, for antifoulant activity. The method and apparatus may also be adapted to test bioactive compounds alone or in combination with other biocides, against any type of fouling organism.

Therefore, while this application has disclosed an example of a laboratory set-up for antifoulant toxicity investigation, it should be reiterated that such apparatus is useful in any field where it is desirable to release at a known release rate a soluble biologically active chemical agent from a surface into a fluid containing an organism which is potentially reactive with the chemical agent. Nothing in this application should be taken to exclude either liquid or gases from use of the word "fluid". Obviously, many modifications and variations of the present invention are possible in light of the above teachings. Thus, it is to be understood that within the scope of the appended claims, the invention may be practiced otherwise than as specifically described herein.

What is claimed is:

1. Apparatus for releasing, at least one known release rate, at least one soluble antifouling agent from a surface into a fluid containing at least one organism potentially reactive with at least one said antifouling agent, comprising:

at least one porous membrane having an inner surface and an exposed surface;

at least one test cell, each said test cell holding one said porous membrane and having a fluid-tight inner area adjacent said inner surface of said porous membrane; and a flow regulator for delivering a solution containing at least one said antifouling agent to each said test cell and perfusing said solution through each said porous membrane from each said inner surface to each said exposed surface at each said known release rate.

2. Apparatus for releasing, at least one known release rate, at least one soluble antifouling agent from a surface into a fluid containing at least one organism potentially reactive with at least one said antifouling agent, comprising:

at least one porous membrane having an inner surface and an exposed surface;

at least one test cell, each said test cell holding one said porous membrane and having a fluid-tight inner area adjacent said inner surface of said porous membrane;

means for introducing said fluid past said each exposed surface; and a flow regulator for delivering a solution containing at least one said antifouling agent to each said test cell and perfusing said solution through each said porous membrane from each said inner surface to each said exposed surface at each said known release rate.

3. Apparatus for releasing at least one soluble biologically active chemical agent from a surface into a fluid as in claim 2, wherein said means for introducing said fluid is controlled.

4. Apparatus for releasing at least one soluble antifouling agent from a surface into a fluid as in claims 1, 2 or 3, wherein at least one said test cell is a modified filter holder.

5. Apparatus for releasing at least one soluble antifouling agent from a surface into a fluid as in claims 1, 2 or 3, wherein at least one said test cell is an aerosol holder.

6. Apparatus for releasing at least one soluble antifouling agent from a surface into a fluid as in claims 1, 2 or 3, wherein said flow regulator is a Marriott bottle.

7. Apparatus for releasing at least one soluble antifouling agent from a surface into a fluid as in claims 1, 2 or 3, wherein said flow regulator is a peristaltic pump.

8. Apparatus for releasing at least one soluble antifouling agent from a surface into a fluid as in claims 1, 2 or 3, wherein the components of said apparatus which are in contact with at least one said antifouling agent are selected from materials which are substantially nonabsorptive and unreactive with said antifouling agent.

9. Apparatus for releasing at least one soluble antifouling agent from a surface into a fluid as in claims 1, 2 or 3, wherein said fluid is a marine organism populated liquid.

10. Apparatus for releasing at least one soluble antifouling agent from a surface into a fluid as in claims 1, 2 or 3, wherein at least one said chemical agent is an antifoulant biocidal agent.

11. Apparatus for releasing at least one soluble antifouling agent from a surface into a fluid as in claim 3, wherein at least one said chemical agent is a biocidal agent.

12. Apparatus for releasing at least one soluble antifouling agent from a surface into a fluid as in claim 3, wherein said means for introducing said fluid past each said exposed surface includes a tank and a rack located within said tank for holding at least one said test cell, whereby said fluid is controllably introduced into said tank and each said test cell is at least partially submersed in said fluid.

13. Apparatus for releasing at least one soluble antifouling agent from a surface into a fluid as in claim 3, wherein said means for introducing said fluid past each said exposed surface includes a tank, a baffle located within said tank for equalizing said fluid when contained within said tank, and a rack located within said tank for holding at least one said test cell, whereby said fluid is controllably introduced into said tank and each said test cell is at least partially submersed in said fluid.

14. Apparatus for releasing at least one soluble antifouling agent from a surface into a fluid as in claim 3, wherein said means for introducing said fluid past each said exposed surface includes an outer tank, an inner tank housed within said outer tank with an interstice between said inner tank and said outer tank, and a rack located within said inner tank for holding at least one said test cell, whereby said fluid is controllably introduced into said inner tank and each said test cell is at least partially submersed in said fluid, any overflow of said fluid from said inner tank being confined to said interstice.

15. Apparatus for releasing at least one soluble antifouling agent from a surface into a fluid as in claim 3, wherein said means for introducing said fluid past each said exposed surface includes an outer tank, an inner tank housed within said outer tank with an interstice between said inner tank and said outer tank, a baffle located within said inner tank for equalizing said fluid when contained within said inner tank, and a rack located within said inner tank for holding at least one said test cell, whereby said fluid is controllably introduced into said inner tank and each said test cell is at least partially submersed in said fluid, any overflow of said fluid from said inner tank being confined to said interstice.

16. Apparatus for releasing at least one soluble antifouling agent from a surface into a fluid as in claim 14, further comprising means for draining said overflow of said fluid.

17. Apparatus for releasing at least one soluble antifouling agent from a surface into a fluid as in claim 15, further comprising means for draining said overflow of said fluid.

18. A method for determining the effect, at each of at least one known release rate from a surface into a fluid, of at least one soluble antifouling agent which is released from said surface into said fluid, upon at least one organism in said fluid, comprising:
  housing a porous membrane within each of at least one test cell, whereby one surface of said membrane is an exposed surface and the other surface of said membrane is an inner surface located adjacent a fluid-tight inner area of said test cell;
  introducing said fluid past each said exposed surface, said fluid containing at least one organism potentially reactive with at least one said antifouling agent;
  delivering a solution containing at least one said antifouling agent to each said test cell and perfusing said solution through each said porous membrane from each said inner surface to each said exposed surface at each said known release rate for a corresponding known period of time; and
  observing reactive effect, for each said known release rate, between at least one said antifouling agent and at least one said organism.

19. A method for determining the effect, at each of at least one known release rate from a surface into a fluid, of at least one soluble antifouling agent which is released from said surface into said fluid, upon at least one organism in said fluid, comprising:
  housing a porous membrane within each of at least one test cell, whereby one surface of said membrane is an exposed surface and the other surface of said membrane is an inner surface located adjacent a fluid-tight inner area of said test cell;
  introducing said fluid past each said exposed surface, said fluid containing at least one organism potentially reactive with at least one said antifouling agent;
  delivering a first solution, containing at least one said antifouling agent, to each said test cell and perfusing said first solution through each said porous membrane from each said inner surface to each said exposed surface at each said known release rate for a corresponding known period of time; and
  delivering a second solution, essentially said first solution absent at least one said antifouling agent, to each said test cell and perfusing said first solution through each said porous membrane from each said inner surface to each said exposed surface at each said known release rate for each said corresponding known period of time; and
  comparing, for each said known release rate, reactive effect between said first solution and at least one said organism with reactive effect between said second solution and each said organism.

20. A method for determining the effect of at least one soluble antifouling agent upon at least one organism as in claims 18 or 19, wherein said fluid is introduced at a controllable flow rate.

21. A method for determining the effect, at each of at least one known release rate from a surface into a fluid, of at least one soluble biologically active antifoulant biocidal chemical agent which is released from said surface into said fluid, upon at least one organism in said fluid, comprising:
  housing a porous membrane within each of at least one test cell, whereby one surface of said membrane is an exposed surface and the other surface of said membrane is an inner surface located adjacent a fluid-tight inner area of said test cell;
  introducing said fluid past each said exposed surface, said fluid being a marine organism populated liquid containing at least one marine organism potentially reactive with at least one said antifoulant agent;
  delivering a first solution, containing at least one said antifoulant agent, to each said test cell and perfusing said first solution through each said porous membrane from each said inner surface to each said exposed surface at each said known release rate for a corresponding known period of time; and
  delivering a second solution, essentially said first solution absent at least one said antifoulant agent, to each said test cell and perfusing said first solution through each said porous membrane from each said inner surface to each said exposed surface at each said known release rate for each said corresponding known period of time; and
  comparing, for each said known release rate, in terms of numbers of selected marine organisms adhering to at least a portion of each said exposed surface of each said membrane, reactive effect between said first solution and at least one said selected marine organism with reactive effect between said second solution and each said selected marine organism.

22. A method for determining the effect of at least one soluble biologically active antifoulant biocidal chemical agent upon at least one organism as in claims 21, wherein said fluid is introduced at a controllable flow rate.

23. A method for determining the effect of at least one soluble biologically active antifoulant biocidal chemical agent upon at least one organism as in claims 21 or 22, further comprising repeating all said steps at least once while varying the concentration of at least one said antifoulant agent for each said repitition.

24. A method for determining the effect of at least one soluble biologically active antifoulant biocidal chemical agent upon at least one organism as in claim 23, further comprising comparing density results obtained from said membrane perfusion of said first solution with density results obtained from said membrane perfusion of said second solution so as to generate a surviving fraction of each said selected marine organism as a decimal percentage relative to controls for each of the repetitions performed.

25. A method for determining the effect of at least one soluble biologically active antifoulant biocidal chemical agent upon at least one organism as in claim 23, further comprising comparing density results obtained from said membrane perfusion of said first solution with density results obtained from said membrane perfusion of said second solution and with density results obtained from at least one nonperfusing membrane so as to generate a surviving fraction of each said selected marine organism as a decimal percentage relative to controls for each of the repetitions performed.

26. A method for determining the effect of at least one soluble biologically active antifoulant biocidal chemical agent upon at least one organism as in claim 24, further comprising preparing a dose-response graph for at least one said antifoulant agent by plotting the logit of the surviving fraction versus the flux data.

27. A method for determining the effect of at least one soluble biologically active antifoulant biocidal chemical agent upon at least one organism as in claim 25, further comprising preparing a dose-response graph for at least one said antifoulant agent by plotting the logit of the surviving fraction versus the flux data.

28. A method for determining the effect of at least one soluble biologically active antifoulant biocidal chemical agent upon at least one organism as in claim 26, further comprising fitting the dose-response graph data with a best form fit line so as to generate a toxicity curve.

29. A method for determining the effect of at least one soluble biologically active antifoulant biocidal chemical agent upon at least one organism as in claim 27, further comprising fitting the dose-response graph data with a best form fit line so as to generate a toxicity curve.

30. A method for determining the effect of at least one soluble biologically active antifoulant biocidal chemical agent upon at least one organism as in claim 28, further comprising selecting a failure criteria by choosing the survival fraction desired and calculating its logit.

31. A method for determining the effect of at least one soluble biologically active antifoulant biocidal chemical agent upon at least one organism as in claim 29, further comprising selecting a failure criteria by choosing the survival fraction desired and calculating its logit.

32. A method for determining the effect of at least one soluble biologically active antifoulant biocidal chemical agent upon at least one organism as in claim 30, further comprising determining the minimum effective release rate for at least one said antifoulant agent by entering said desired logit on said dose-response graph and reading from said toxicity curve the corresponding flux required.

33. A method for determining the effect of at least one soluble biologically active antifoulant biocidal chemical agent upon at least one organism as in claim 31, further comprising determining the minimum effective release rate for at least one said antifoulant agent by entering said desired logit on said dose-response graph and reading from said toxicity curve the corresponding flux required.

34. Apparatus for releasing at least one soluble antifouling agent from a surface into a fluid as in claim 4, wherein the components of said apparatus which are in contact with at least one said antifouling agent are selected from materials which are substantially nonabsorptive and unreactive with said antifouling agent.

35. Apparatus for releasing at least one soluble antifouling agent from a surface into a fluid as in claim 5, wherein the components of said apparatus which are in contact with at least one said antifouling agent are selected from materials which are substantially nonabsorptive and unreactive with said antifouling agent.

36. Apparatus for releasing at least one soluble antifouling agent from a surface into a fluid as in claim 6, wherein the components of said apparatus which are in contact with at least one said antifouling agent are selected from materials which are substantially nonabsorptive and unreactive with said antifouling agent.

37. Apparatus for releasing at least one soluble antifouling agent from a surface into a fluid as in claim 7, wherein the components of said apparatus which are in contact with at least one said antifouling agent are selected from materials which are substantially nonabsorptive and unreactive with said antifouling agent.

38. Apparatus for releasing at least one soluble antifouling agent from a surface into a fluid as in claims 1, 2 or 3, wherein at least one said membrane is microporous.

39. A method for determining the effect of at least one soluble biologically active antifoulant biocidal chemical agent upon at least one organism as in claim 21, further comprising:
repeating all said steps at least once while varying the concentration of at least one said antifoulant agent for each said repitition;
preparing a plurality of said first solutions, prior to delivering and perfusing each said first solution, by dissolving at least one said antifoulant agent in an alcohol solution so as to create a stock solution, pasteurizing and filtering seawater, and serially diluting said stock solution with said seawater so as to create said plurality of said first solutions at varying concentrations of at least one said antifoulant agent;
preparing at least one said second solution, prior to delivering and perfusing each said second solution, by pasteurizing and filtering seawater and diluting said filtering seawater with said alcohol solution, so as to create at least one control solution having essentially the same composition, absent at least one said antifoulant agent, as each said first solution.

40. A method for determining the effect of at least one soluble biologically active antifoulant biocidal chemical agent upon at least one organism as in claim 22, further comprising:
repeating all said steps at least once while varying the concentration of at least one said antifoulant agent for each said repetition;
preparing a plurality of said first solutions, prior to delivering and perfusing each said first solution, by dissolving at least one said antifoulant agent in an alcohol solution so as to create a stock solution, pasteurizing and filtering seawater, and serially diluting said stock solution with said seawater so as to create said plurality of said first solutions at varying concentrations of at least one said antifoulant agent;

preparing at least one said second solution, prior to delivering and perfusing each said second solution, by pasteurizing and filtering seawater and diluting said filtering seawater with said alcohol solution, so as to create at least one control solution having essentially the same composition, absent at least one said antifoulant agent, as each said first solution.

* * * * *